United States Patent [19]

Bergthaller

[11] Patent Number: 6,043,017
[45] Date of Patent: Mar. 28, 2000

[54] COLOR PHOTOGRAPHIC SILVER HALIDE MATERIAL

[75] Inventor: Peter Bergthaller, Bergisch Gladbach, Germany

[73] Assignee: Agfa-Gevaert NV, Belgium

[21] Appl. No.: 09/339,623

[22] Filed: Jun. 24, 1999

[30] Foreign Application Priority Data

Jul. 4, 1998 [DE] Germany .......................... 198 29 978

[51] Int. Cl.$^7$ ..................................... G03C 1/73
[52] U.S. Cl. .......................... 430/558; 430/384; 430/385
[58] Field of Search ............................................ 430/558

[56] References Cited

U.S. PATENT DOCUMENTS 3,277,086  10/1966  Wei et al. ................................... 544/9

FOREIGN PATENT DOCUMENTS 398 664    11/1990  European Pat. Off. .
563 985    10/1993  European Pat. Off. .
40 16 418  11/1991  Germany .

OTHER PUBLICATIONS

J.W. Chern, et al., "1,2,4–Benzothiadiazine 1,1–Dioxides, Part 4:Mitsunobu Reactions of 3–Hydroxylalkylamino–and 3–Mercaptoalkylamin–4H–1,2,4–benzothiadiazine 1,1–Dioxides. A Convenient Synthesis of Built–in Guanidine Tricycles and Disulfides" Synthesis, Bd. 2, Feb. 1991,(1991–02) pp. 159–161).

S. Plescia et al., "Reductive Heterocycliczation Leading to Some 9,9–Dioxy–4H–pyrazolo(1,5–b)–1,2,4–benzothiadiazine Derivatives", Journal of Heterocyclic Chemistry. Bd. 13, Nr. 4, Apr. 1976 (1976–04) pp. 395–397.

*Primary Examiner*—Hoa Van Le
*Attorney, Agent, or Firm*—Connelly Bove Lodge & Hutz LLP

[57] ABSTRACT

The present invention relates to a new compound of formula (I)

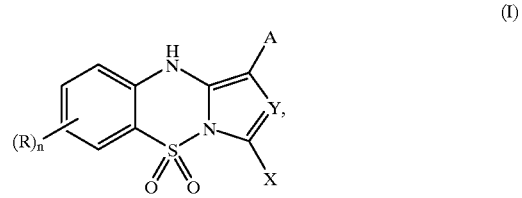

with the proviso that Y represents N, and also relates to a colour photographic silver halide material comprising at least one red-sensitive silver halide layer with which according to the invention a compound of formula (I) is associated, and also relates to a photographic colour development process in which couplers of formula (I) are reacted with colour developers of the phenylenediamine and/or diaminotoluene type to form coupling products which exhibit a strong absorption, particularly in the infrared region. The present invention further relates to the use of compounds of formula (I) as cyan and/or infrared couplers in colour photographic silver halide materials.

13 Claims, No Drawings

COLOR PHOTOGRAPHIC SILVER HALIDE MATERIAL

This invention relates to new compounds of formula (I), with the proviso that Y represents N, and to a colour photographic silver halide material comprising at least one red-sensitive silver halide layer with which according to the invention a compound of formula (I) is associated, and also relates to a photographic colour development process in which couplers of formula (I) are reacted with colour developers of the phenylenediamine and/or diaminotoluene type to form coupling products which exhibit a strong absorption, particularly in the infrared region. The present invention further relates to the use of compounds of formula (I) as cyan and/or infrared couplers in colour photographic silver halide materials.

In practice, many demands are made on colour couplers and on the dyes obtained therefrom by chromogenic development. Thus the rate of coupling of colour couplers with the oxidation product of the colour developer should be high, and dye formation should occur with a high yield. Colour couplers and the dyes obtained therefrom have to be sufficiently stable in relation to light, elevated temperatures and moisture. This applies both to unexposed material and to processed material. For example, any residual couplers which are still present in the white regions of the image of the processed material must not discolour. Moreover, the dyes should be sufficiently resistant to gaseous reducing or oxidising agents. In addition, unless this is expressively provided otherwise, they have to be incorporated in a diffusion-resistant manner, and during chromogenic development the dye should be deposited in dissolved form as far as possible, or at least not in the form of coarse dispersions. In particular, the absorption of the dye should not become blurred or shifted towards shorter wavelengths due to the formation of dye aggregates. Moreover, the mechanical properties of the layers must not be impaired by the incorporation of colour couplers.

Finally, the dyes produced from colour couplers during chromogenic development should exhibit an absorption curve with a maximum which corresponds as accurately as possible to the colour of the subtractive partial image concerned, and should exhibit secondary absorptions which are as low as possible. In colour films, the absorption maxima of the image dyes should also correspond as accurately as possible to the sensitisation maxima of the colour print materials used for copying.

Compounds which are used as cyan couplers, i.e. as colour couplers which are suitable for the production of the cyan partial image, are generally derived from phenol or from α-naphthol. Apart from these, cyan couplers of the imidazole type are also known. Examples of colour couplers comprising an uncondensed imidazole ring include 2,4-disubstituted and 4,5-disubstituted imidazoles, particularly those which are known from the following patent specifications: GB 1,545,507, EP 0 249 453, EP 0 304 856 and U.S. Pat. No. 5,051,347. However, these known cyan couplers do not exhibit the aforementioned features to a sufficient extent. In particular, the absorption behaviour in the infrared region of the dyes formed from prior art cyan couplers within the scope of conventional development is not satisfactory. Moreover, the coupling capacity is often not satisfactory. There is therefore a continuing need for cyan couplers which exhibit as many of the aforementioned properties as possible, and which in particular result in coupling products which also exhibit an absorption in the infrared region. Colour couplers from the 1-naphthol-2-carboxylic acid amide series are known from the prior art; after coupling with conventional developers these colour couplers form dyes with a satisfactory absorption in the infrared region.

In addition, colour couplers from the class comprising imidazo[5,1-c]benzothiadiazine-S,S-dioxides are known, from DE 40 16 418 for example, as photographic colour couplers for the production of violet to cyan colour images. These couplers are difficultly soluble, however, and the azomethine dyes obtained exhibit secondary absorptions.

The underlying object of the present invention is to provide cyan couplers which after coupling with the usual developer oxidation products are distinguished by a particularly intensive absorption in the infrared region, especially by an absorption in the region of 680 to 750 nm. The object is also to achieve a shift of the absorption bands towards longer wavelengths after coupling with conventional developers, compared with the cyan couplers which are known from the prior art. At the same time, the object is to provide couplers which are readily capable of being incorporated in the photographic silver halide material and which are distinguished there by their high resistance to light in particular.

Surprisingly, it has been found that the compounds of formula (I) described below are outstandingly suitable as cyan or infrared couplers, and that in particular the dyes formed with conventional developers exhibit a significant absorption in the infrared. The dyes which are obtained as a result of chromogenic coupling with developers of the phenylenediamine and/or diaminotoluene type exhibit absorption maxima within the range from 680 to 750 nm, particularly from 700 to 740 nm. At the same time, the couplers themselves, as well as the cyan and/or infrared dyes obtained, possess a high resistance to light and moisture.

The present invention relates to compounds of formula (I)

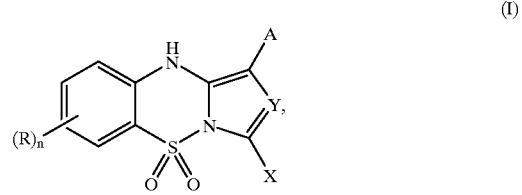

wherein

A denotes an electron acceptor group with a $\sigma_{p-}$ value of >0.25,

R denotes a substituent, n denotes 0, 1, 2, 3 or 4,

Y denotes N and

X denotes H or a group which is separable during chromogenic coupling.

These compounds are suitable, for example, for use in photographic materials or as couplers for the production of azo dyes or methine dyes, by reaction with diazonium salts or aldehydes for example.

The present application further relates to a colour photographic silver halide material comprising at least one blue-sensitive silver halide emulsion layer which contains least one yellow coupler, at least one green-sensitive silver halide emulsion layer which contains at least one magenta coupler, and at least one red-sensitive silver halide emulsion layer which contains at least one cyan coupler, characterised in that a compound of formula (I) is associated with the red-sensitive layer,

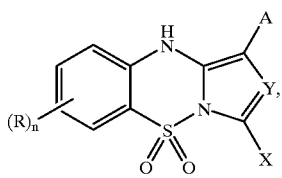

(I)

wherein

A denotes an electron acceptor group with a $\sigma_{p\text{-}}$ value of >0.25, R denotes a substituent, n denotes 0, 1, 2, 3 or 4, Y denotes N or C—CN, and X denotes H or a group which is separable during chromogenic coupling.

Compounds which are particularly preferred in this respect are those in which Y denotes N.

n preferably denotes 0, 1 or 2. The substituents may be the same or different. A substituent in the sense of the present Application is to be understood, for example, to include halogens such as F, Cl or Br in particular, and also alkoxy, alkylthio, aryloxy, arylthio, acylamino, alkylsulphonamido, alkylsulphamoyl, alkylcarbamoyl, arylsulphon-amido, arylsulphamoyl, arylcarbamoyl, alkyl, alkenyl, aryl, hetaryl, arylene, hetarylene, alkylene, alkoxycarbonyl, ureido or cyano groups. The preferred examples of the groups represented by R are: —CN, —Cl, —OR$^1$, —NR$^2$CO—O R$^1$, —CONH R$^1$, —COO R$^1$ and —S R$^1$. In the sense of the present invention, R$^1$ can represent an alkyl, aryl, arylene, hetaryl or hetarylene group. R$^1$ is most preferably a methyl, ethyl, propyl, isopropyl, butyl, isobutyl or a secondarily branched alkyl group comprising 6 to 30 C atoms. Perfluorinated alkyl groups, such as trifluoromethyl, pentafluoroethyl, heptafluoropropyl and nonafluorobutyl for example, are particularly preferred. Other preferred groups include substituted and unsubstituted cycloalkyl groups, particularly cyclohexane groups, and also substituted and unsubstituted aryl groups, particularly phenyl groups. R$^2$ preferably represents H or an alkyl radical.

Alkyl in the sense of the present application is to be understood to mean linear or branched, cyclic or straight chain, substituted or unsubstituted hydrocarbon groups. These are preferably alkyl groups comprising 1 to 20 C atoms. Open-chain alkyl groups which are particularly suitable include methyl, ethyl, n-propyl, n-butyl, n-decyl, n-dodecyl, n-tetradecyl, n-hexadecyl and n-octadecyl, as well as branched alkyl radicals, particularly 2-hexyldecyl and 2-ethylhexyl radicals. The preferred cycloalkyl groups are cyclohexyl groups, particularly 4-t-butyl cyclohexyl and 2,6-di-t-butyl-4-methylcyclohexyl groups.

Alkenyl in the sense of the present invention is to be understood to mean linear or branched, cyclic or straight chain, substituted or unsubstituted unsaturated hydrocarbon radicals, such as ethenyl, 2-propenyl or isopropenyl for example.

Aryl in the sense of the present Application is to be understood to mean aromatic hydrocarbon groups, wherein these are preferably 5- or 6-membered ring systems which may exist as monocyclic or as condensed ring systems. These ring systems may comprise both substituted and unsubstituted ring systems. Phenyl and naphthyl groups are particularly preferred, for example.

Hetaryl in the sense of the present Application is to be understood to mean aromatic systems which contain at least one hetero atom. These are preferably 5- or 6-membered ring systems which may exist as monocyclic or as condensed ring systems. These ring systems may comprise both substituted and unsubstituted ring systems. N, S and O are particularly suitable as hetero atoms. A ring system may preferably contain between 1 and 3 hetero atoms, wherein these may be the same or different hetero atoms. In condensed ring systems, a plurality of the same or different heterocyclic systems can be condensed, such as hetaryl systems with aryl systems. Typical examples include pyridine, pyridazine, pyrimidine, pyrazine, oxazole, isoxazole, thiazoles, 1,3,4-oxydiazol, 1,2,4-oxydiazol, imidazole, 1,2,3-triazole and 1,2,4-triazole.

According to the invention, an electron acceptor group represented by A has a value of the Hammett substituent constant $\sigma_p$ (for the definition of this constant see Hansch et al. J. Med. Chem. 1973, 16, 1207 and ibid. 1977, 20. 304) which is higher than 0.25, preferably higher than 0.3 and which in particular is higher than 0.45. Examples of substituents of this type include a keto group, an acetal group, a carboxylic acid ester group, a carbonamide group, a cyano group, a sulphonamide group, an acylurea group, a sulphonylcarbamoyl group, a sulphamoylcarbamoyl group, an open or cyclic amidine group, a cyclic amidrazone group, a heterocyclic radical with an electron acceptor character which is bonded via a C atom or via an N atom, e.g. a pyridyl group, a pyridazinyl group, a pyrimidinyl group, a triazinyl group, a pyrazinyl group, an imidazole radical, a triazole radical, an oxazol radical, a 1,2,4-oxydiazol radical or a 1,3,4-oxydiazol radical, a thiophene radical, a thiazole radical, a thiazolone radical, a thiadiazole radical, a phosphonic acid ester radical, a sulphoxide group, a sulphone group, a sulphilimine group or a sulphoximine group. The group represented by A is most preferably an alkoxycarbonyl, carbamoyl or cyano group.

Examples of substituents X which are suitable according to the invention include H or organic groups which are generally linked to the coupling site via a sulphur, oxygen or nitrogen atom, wherein the leaving group may give rise to special photographic effects. If the leaving group is a cyclic group, it can be linked to the coupling site of the coupler molecule either directly via an atom which is a constituent of a ring, e.g. a nitrogen atom, or it can be linked indirectly via a member interposed therebetween. Large numbers of separable groups of this type are known, e.g. as volatile groups of two-equivalent couplers. The group which is separated may also be a colour coupler or a white coupler itself.

Examples of leaving groups which are linked via oxygen are those corresponding to the formula

—OR$^3$, wherein R$^3$ represents an acyclic or cyclic organic radical, e.g. an alkyl, an aryl, an heterocyclic group or an acyl, which may be derived from an organic carboxylic acid or sulphonic acid. In separable groups of this type which are particularly preferred, R$^3$ denotes a phenyl group which is optionally substituted. Examples of groups such as these are described in U.S. Pat. No. 3,408,194 and DE-A 24 56 076.

Examples of separable groups which are linked via nitrogen are described in the following German Patents:

DE-A 20 57 941, DE-A 21 63 812, DE-A 22 13 461, DE-A 22 19 917, DE-A 22 61 361 , DE-A 22 63 875, DE-A 23 18 807, DE-A 23 29 587, DE-A 23 44 155, DE-A 23 63 675, DE-A 24 33 812, DE-A 24 41 779, DE-A 24 42 703, DE-A 25 28 638, DE-A 25 28 860, DE-A 26 37 817, DE-A 28 18 373, DE-30 20 416.

Without exception, these are 5- or 6-membered heterocyclic rings which are bonded to the coupling site of the coupler via a ring nitrogen atom. These heterocyclic rings often contain groups which enhance their acidity, e.g. carbonyl or sulpho groups or double bonds, adjacent to the nitrogen atom which is responsible for the bonding to the coupler molecule. Hydantoins are typical examples thereof.

According to the invention, a radical which is separable during chromogenic development and which is represented by X may preferably be H, a halogen, particularly Cl, Br or F, or an alkoxy, aryloxy, hetaryloxy, acyloxy, sulphonyloxy, alkoxycarbonyloxy, aryloxycarbonyloxy, alkylthio, arylthio, hetarylthio, alkoxycarbonylthio, acylalkylamino, alkoxycarbonylamino, N-alkylsulphonamido, aryloxycarbonylamino or carboxy substituent, as well as a heterocyclic radical which is bonded via a nitrogen atom, or an arylazo or hetarylazo group.

A group which is separable under the conditions of chromogenic development and which is represented by X in formula (I) may also preferably be the residue of a photographically active compound. The following compounds are to be understood as photographically active compounds in the sense of the present invention, for example: development inhibitors, bleaching inhibitors, bleaching accelerators, development accelerators, a nucleating agent which forms a silver nucleus, a soluble mercaptan compound which promotes complete development, stabilisers, white couplers, scavengers, auxiliary developer substances which are suitable for electron transfer, e.g. those of the phenidone type, or colour coupler or white coupler compounds.

Development inhibitors which are particularly suitable are those from the series comprising benzotriazoles, thienotriazoles, monocyclic 1,2,3-triazoles, monocyclic 1,2,4-triazoles, 1-aryl-5-mercaptotetrazoles, 1-alkyl-5-mercaptotetrazoles, 2-mercapto-5-alkylthio-1,3,4-thiadiazoles, as well as 2-mercapto-5-alkylthio-1,3,4-oxadiazoles.

In addition, however, X can also represent a group which is composed of a timing group and of the residue, which is bonded thereto, of a photographically active compound. A group which is described as a timing group is a group which, after it has separated from the coupling site of the coupler during the coupling thereof with the oxidation product of the colour developer, is capable of releasing a residue of a photographically active compound in a subsequent reaction. In many cases, the residue of the photographically active compound which is bonded thereto is released and becomes effective after some delay.

Timing groups include
the —O—CH(R)— groups which are described in DE-A-2 803 145, in which the O atom is bonded to the coupling site of the coupler and the C atom is bonded to an N atom of a photographically useful group, which after separation from the coupler can be released in a rapid intramolecular or intermolecular nucleophilic displacement reaction (e.g. DE-A 2 855 697);

groups in which electron transfer can occur along a conjugated system after separation from coupler, whereby the release of the photographically useful group is likewise utilised (e.g. in DE-A 3 105 026)

or a —V—C(=NR)— group, wherein V (e.g. —O—) is bonded to the coupling site of the coupler and the C atom is bonded to an atom of the photographically useful compound, and wherein R represents an aryl for example (e.g. in EP-A 0 127 063).

The timing group can also be a group which after separation from the coupling site of the coupler can itself participate in a redox reaction or a coupling reaction, and which as a consequence of such a reaction itself releases a photographically useful group which is bonded to it.

The colour couplers which are used according to the invention are preferably provided with a ballast radical. Ballast radicals are radicals which enable the colour couplers according to the invention to be incorporated in the hydrophilic binders which are usually employed. Organic radicals which are most suitable and which are preferably used for this purpose generally contain straight chain or branched aliphatic groups and optionally also contain carbocyclic or heterocyclic aromatic groups, which generally comprise 8 to 20, preferably 12 to 18 C atoms. R in formula (I) may represent a ballasting group, for example, but the ballasting group is preferably a constituent of group A. The ballasting groups which are particularly preferred are open-chain or cyclic, branched or unbranched hydrocarbons comprising 2 to 18 C atoms.

Examples of cyan and/or infrared couplers which can be used according to the invention are listed below.

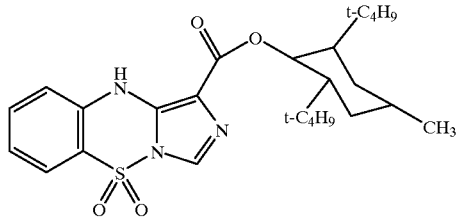

IRC-1

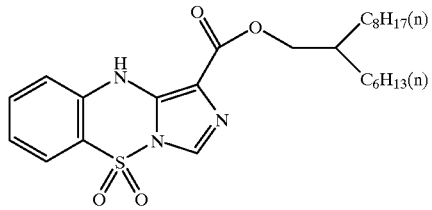

IRC-2

-continued
IRC-3
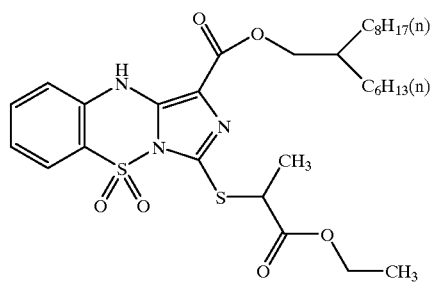
IRC-4
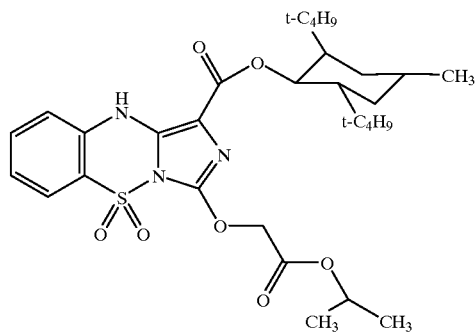
IRC-5
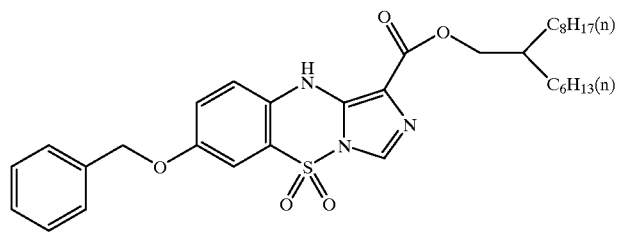
IRC-6
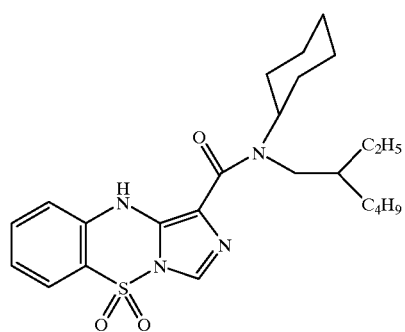
IRC-7
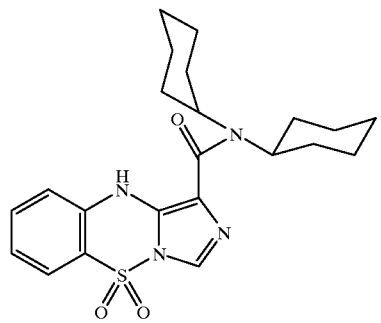

-continued
IRC-8
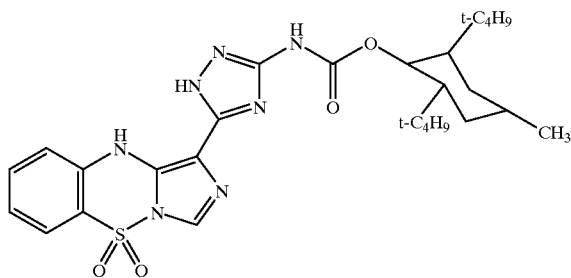
IRC-9
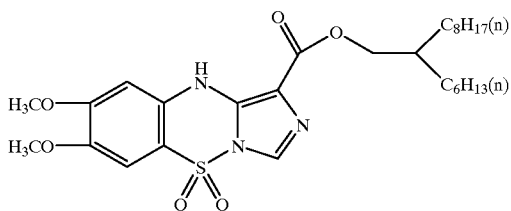
IRC-10
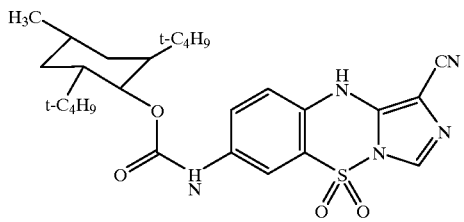
IRC-11
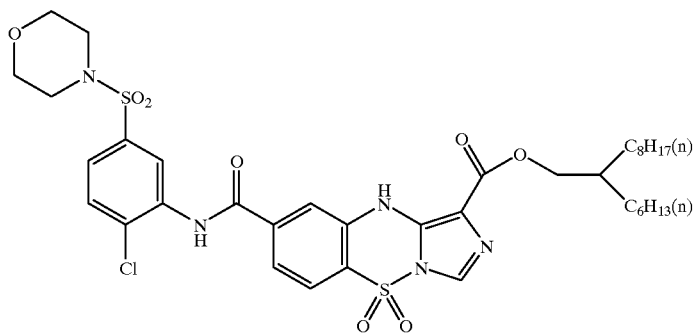
IRC-12
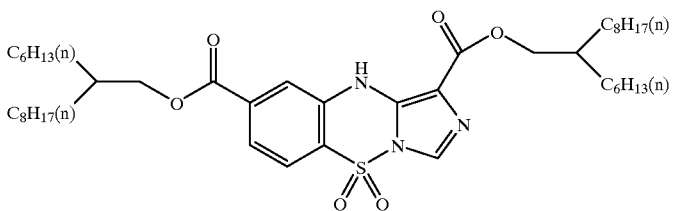
IRC-13
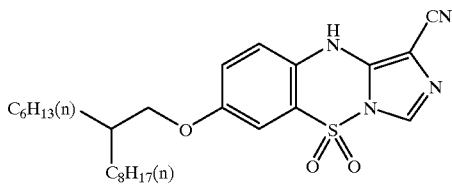

-continued
IRC-14
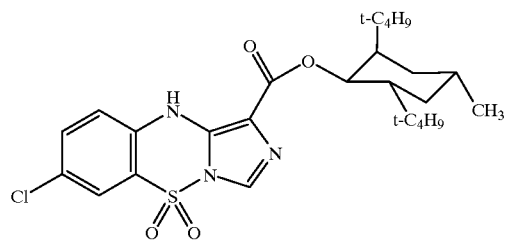
IRC-15
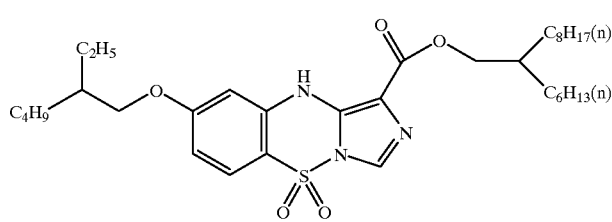
IRC-16
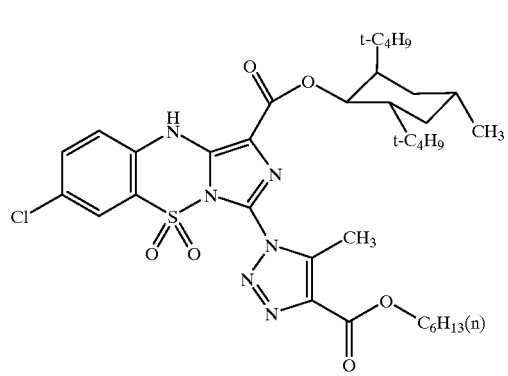
IRC-17
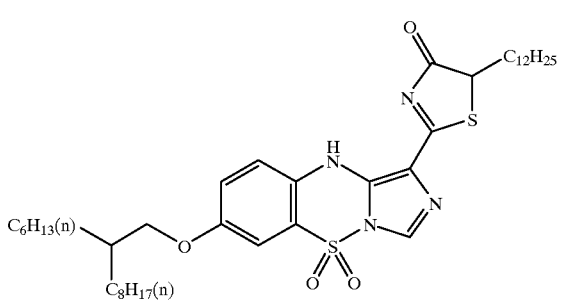
IRC-18
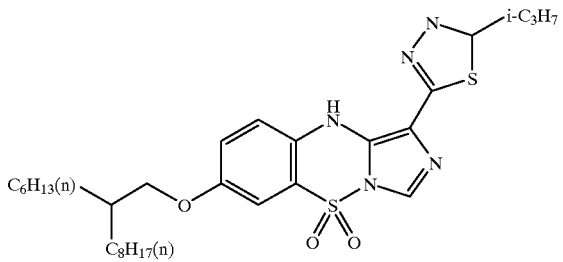

-continued
IRC-19
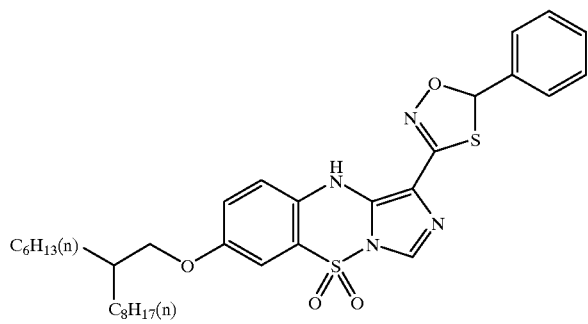
IRC-20
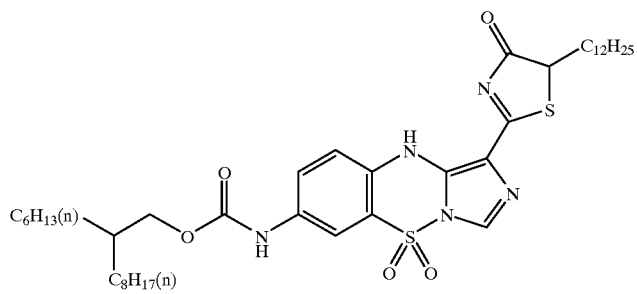
IRC-21
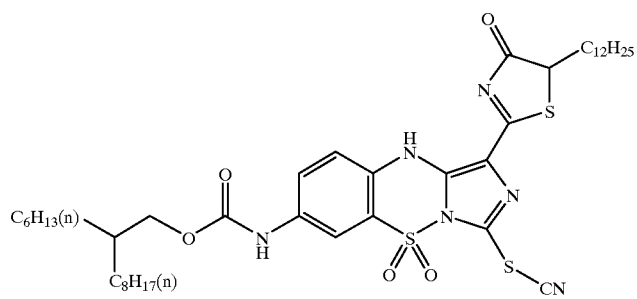
IRC-22
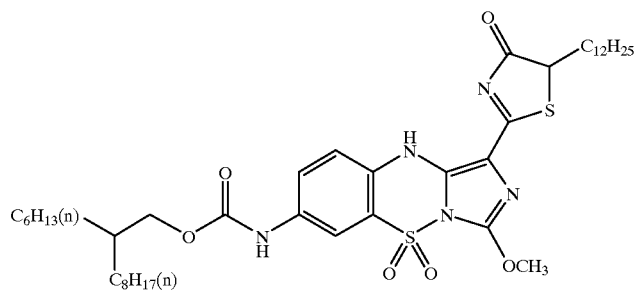
IRC-23
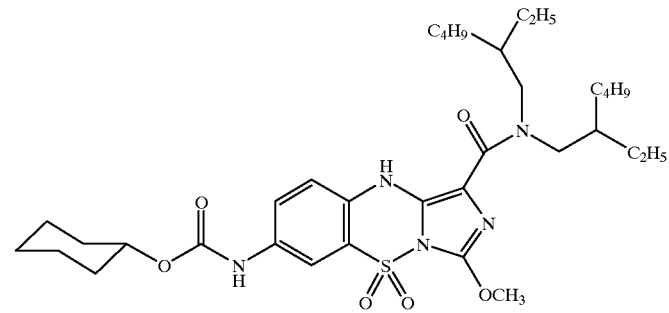

IRC-24

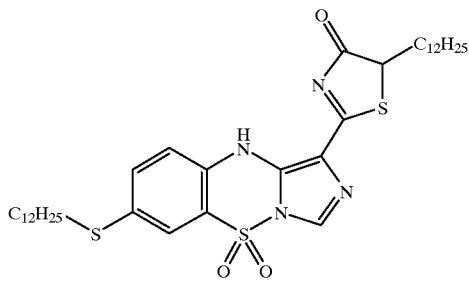

IRC-25

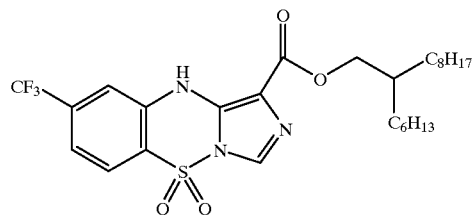

By comparison with the cyan couplers which are known from DE 40 16 418 and which are disclosed as corresponding to formulae (25) and (26) (imidazo[5,1-c] benzothiadiazine-S,S-dioxides), the imidazo[5,1-b] benzothiadiazine-S,S-dioxides according to the invention are distinguished by their higher stability and by their better coupling capacity, which comprises both a higher rate of coupling and better conversion. In particular, the azomethine dyes which can be obtained from these new colour couplers exhibit a main band which absorbs at a longer wavelength within the range from 680 to 750 nm.

Depending on the constitution and the substituents of the colour couplers according to the invention, and depending in particular on the constituent ring, numerous methods are available for the synthesis thereof. In particular, it has been shown that the cyclisation methods described in DE 40 16 418 are suitable, provided that work-up is not effected under alkaline conditions as described there, but is effected under acid conditions. If the large amounts of hydrogen chloride which are evolved in the methods described in DE 40 16 418 are not bound by acid-binding media, compounds corresponding to formula (I) are obtained. Compared with the method described in DE 40 16 418, it is not essential for the production of the couplers according to the invention for work-up (during which ring opening occurs) always to be effected under acidic conditions. A pH of <3, particularly <2, should preferably be maintained.

In addition, the colour photographic material according to the invention may contain compounds which, for example, are capable of releasing a development inhibitor, a development accelerator, a bleaching accelerator, a developer, a solvent for silver halide, a fogging agent or an anti-fogging agent. Examples thereof include what are termed DIR hydroquinones or other compounds such as those described in U.S. Pat. No. 4,636,546, U.S. Pat. No. 4,345,024, U.S. Pat. No. 4,684,604 and in DE-A 24 47 079, DE-A 25 15 213 and DE-A 31 45 640 or in EP-A 198 438 for example. These compounds perform the same function as DIR, DAR or FAR couplers, except that they do not form coupling products.

Examples of high molecular weight colour couplers are described in DE-C 1 297 417, DE-A 24 07 569, DE-A 31 48 125, DE-A 32 17 200, DE-A 33 20 079, DE-A 33 24 932, DE-A 33 31 743, DE-A 33 40 376, EP-A 27 284 and U.S. Pat. No. 4,080,211 for example. Colour couplers of high molecular weight are generally produced by the polymerisation of ethylenically unsaturated colour coupler monomers. They can also be obtained by addition polymerisation or condensation polymerisation, however.

The colour couplers according to the invention can be incorporated in silver halide emulsion layers by first preparing a solution or a dispersion of the compound concerned and then adding this to the casting solution for the layer concerned. The choice of a suitable solvent or dispersing agent depends on the solubility of the compound.

Methods of incorporating compounds which are substantially insoluble in water by grinding processes are described in DE-A 26 09 741 and DE-A 26 09 742 for example.

Hydrophobic compounds can also be incorporated in the casting solution by using high-boiling solvents termed oil-formers. Examples of corresponding methods are described in U.S. Pat. No. 2,322,027, U.S. Pat. No. 2,801,170 and EP-A 0 043 037. Instead of low molecular weight oil-formers, oligomers or polymers which possess suitable solvent properties can also be used. The couplers according to the invention are preferably of a hydrophobic nature.

The compounds can also be incorporated in the casting solution in the form of what are termed loaded lattices. Reference is made in this context, for example, to DE-A 25 41 230, DE-A 25 41 274, DE-A 28 35 856, EP-A 0 014 921, EP-A 0 069 671, EP-A 0 130 115, U.S. Pat. No. 4,291,113. The diffusion-resistant incorporation of anionic compounds which are soluble in water (e.g. couplers or dyes) can also be effected by means of cationic polymers termed polymeric mordants.

Examples of suitable oil-formers include alkyl esters of phthalic acid, phosphoric acid esters, phosphonic acid esters, citric acid esters, lactic acid esters, benzoic acid esters, fatty acid esters, amides, alcohols, phenols, sulphonamides, aniline derivatives and hydrocarbons.

The present invention further relates to a photographic colour development process in which a colour photographic material, which contains a compound of formula (I) in at least one silver halide emulsion which is exposed image by image, is developed with a colour developer compound of the phenylenediamine and/or diaminotoluene type.

Typical colour developer compounds which can be used in the sense of the colour development process according to the invention and residues of which are found again in the completely coupled dye are those of the phenylenediamine and/or diaminotoluene series, such as 1-(N-ethyl-N-methanesulphonamido-ethyl)-3-methyl-p-phenylenediamine (CD-3), 1-(N-ethyl-N-hydroxyethyl)-3-methyl-p-phenylenediamine (CD-4), 1-(N-isopropyl-N-methanesulphonamidoethyl)-3-methyl-p-phenylenediamine, 1-(N-isopropyl-N-hydroxyethyl)-3-methyl-p-phenylenediamine, 1-(N-ethyl-N-3-hydroxypropyl)-3-methyl-p-phenylenediamine and N-ethyl-N-4-sulphobutyl-3-methyl-p-phenylenediamine. Other colour developers which can be used as described in J.Am.Chem.Soc. 73, 3106 (1951) for example.

In the process according to the invention, a colour photographic material, which contains at least one silver halide emulsion which has been exposed image by image, is preferably developed using a colour developer compound of the CD3 or CD4 type. The colour couplers according to the invention are contained in the material in spatial and spectral association with a colour-sensitised, light-sensitive silver halide emulsion.

In this connection, the term "spatial association" is to be understood to mean that the colour coupler is present in a spatial relationship to the silver halide layer concerned such that an interaction between them is possible which enables a correspondence of image to be obtained between the silver image formed during development and the colour image produced from the colour coupler. This is generally achieved by the colour couplers being contained in the silver halide emulsion layer itself or in a binder layer which is adjacent thereto and which is optionally light-insensitive.

The term "spectral association" is to be understood to mean that the spectral sensitivity of the light-sensitive silver halide emulsion concerned and the colour image produced from the spatially associated colour coupler are in a defined relationship to each other, wherein a partial colour image of a complementary colour (cyan, magenta, yellow) is normally associated with the spectral sensitivity of each individual chromatic component (red, green, blue). Accordingly, the colour formed from the cyan and/or infrared couplers according to the invention is preferably associated with a red-sensitised silver halide emulsion layer.

With state of the art colour developers, the compounds of formula (I) which are used according to the invention produce dyes, the absorption of which is either very close to the boundary of the infrared region or is already situated therein, preferably within the range from 680 to 750 nm, particularly 700 to 730 nm. Couplers which couple to form dyes with an absorption close to 700 nm are outstandingly suitable as cyan couplers for CN films. Those which couple to form dyes with an absorption higher than 700 nm can be used as infrared couplers or as what are termed functional couplers, i.e. they are capable of splitting off a photographically active group, but make no appreciable contribution to the impression of the colour image. However, it is also possible to use them for the production of coded information, preferably in the paper, which is not visually perceptible in the image. Data on the origin of the image or copyright information can be encoded in this manner, for example. In this case, the spectral or spatial association is linked to special functions of the coupler. In the case of DIR couplers, spectral or spatial association is effected according to functional aspects. It is useful, for example, to dispose a DIR coupler according to the invention in a separate layer under the red-sensitive layer stack or layer constituent.

The present invention also relates to the use of compounds of formula (I) as cyan or infrared couplers in colour photographic silver halide materials.

Examples of colour photographic materials include colour negative films, colour reversal films, colour positive films, colour photographic paper, colour reversal photographic paper, and colour-sensitive materials for the colour diffusion transfer process or the silver halide bleaching process. A review of typical colour photographic materials, and of preferred embodiments thereof and processing methods, is given in Research Disclosure 37038 (February 1995).

Photographic materials consist of a support on which at least one light-sensitive silver halide emulsion layer is deposited. Thin films and foils are particularly suitable as supports. A review of support materials and of the auxiliary layers which are deposited on the front and back thereof is given in Research Disclosure 37254, Part 1 (1995), page 285.

Colour photographic materials usually contain at least one red-sensitive, at least one green-sensitive and at least one blue-sensitive silver halide emulsion layer, and optionally contain intermediate layers and protective layers also.

Depending on the type of photographic material, these layers may be arranged differently. This will be illustrated for the most important products:

Colour photographic films such as colour negative films and colour reversal films comprise, in the following sequence on their support: 2 or 3 red-sensitive, cyan-coupling silver halide emulsion layers, 2 or 3 green-sensitive, magenta coupling silver halide emulsion layers, and 2 or 3 blue-sensitive, yellow-coupling silver halide emulsion layers. The layers of identical spectral sensitivity differ as regards their photographic speed, wherein the less sensitive partial layers are generally disposed nearer the support than are the more highly sensitive partial layers.

A yellow filter layer is usually provided between the green-sensitive and blue-sensitive layers, to prevent blue light from reaching the layers underneath.

The options for different layer arrangements and their effects on photographic properties are described in J. Inf. Rec. Mats., 1994, Vol. 22, pages 183–193.

Colour photographic paper, which as a rule is less sensitive to light than is colour photographic film, usually comprises the following layers on the support, in the following sequence: a blue-sensitive, yellow-coupling silver halide emulsion layer, a green-sensitive, magenta coupling silver halide emulsion layer, and a red-sensitive, cyan-coupling silver halide emulsion layer; the yellow filter layer can be omitted.

Deviations from the number and arrangement of the light-sensitive layers may be effected in order to achieve defined results. For example, all the high-sensitivity layers may be combined to form a layer stack and all the low-sensitivity layers may be combined to form another layer stack in a photographic film, in order to increase the sensitivity (DE 2530645).

The essential constituents of the photographic emulsion layer are binders, silver halide grains and colour couplers.

Information on suitable binders is given in Research Disclosure 37254, Part 2 (1995), page 286.

Information on suitable silver halide emulsions, their production, ripening, stabilisation and spectral sensitisation, including suitable spectral sensitisers, is given in Research Disclosure 36544 (September 1994), in Research Disclosure 37254, Part 3 (1995), page 286, and in Research Disclosure 37038, Part XV (1995), page 89.

Photographic materials which exhibit camera-sensitivity usually contain silver bromide-iodide emulsions, which may also optionally contain small proportions of silver chloride. Photographic copier materials contain either silver chloride-bromide emulsions comprising up to 80 mole % AgBr, or silver chloride-bromide emulsions comprising more than 95 mole % AgCl.

Photographic emulsions can be spectrally sensitised using methine dyes or other dyes. Dyes which are particularly suitable include cyanine dyes, merocyanine dyes and complex merocyanine dyes. Compounds of this type, particularly merocyanines, can also be used as stabilisers.

A review of polymethine dyes which are suitable as spectral sensitisers, on suitable combinations thereof and on combinations having a super-sensitising effect in particular is given in Research Disclosure 17643 (1978), Section IV, and in Research Disclosure 18716 (1979), page 648 (right-hand column) to page 649 (right-hand column).

In addition, pentamethine cyanines which contain naphthothiazole, naphthoxazole or benzthiazole as basic terminal groups can be used as red-sensitisers. These compounds can be substituted with halogen, methyl or methoxy groups and can comprise 9,11-alkylene bridges, particularly 9,11-neopentylene bridges as described in GB 604 217 and BE 660 948. As described in EP 0 532 042, the N,N'-substituents can also be $C_4$–$C_8$ alkyl groups. In addition, the methine chain can comprise substituents such as those mentioned in EP 0 532 042. Pentamethines which comprise only one methyl group on the cyclohexene ring can also be used, as described in EP 0 532 042. As described in BE 660 948, the red-sensitiser can be super-sensitised and stabilised by the addition of heterocyclic mercapto compounds.

The red-sensitive layer can be additionally spectrally sensitised between 390 and 590 am, preferably at 500 nm, as described in AG 5850/5851, so as to achieve an improved differentiation between red tones in accordance with EP 0 304 297, U.S. Pat. No. 806,460 and U.S. Pat. No. 5,084,374.

Compounds of this type, particularly merocyanines, can also be used as stabilisers.

Spectral sensitisers can be added to the photographic emulsion in dissolved form or as dispersions. Both the solutions and the dispersions may contain additives such as wetting agents or buffers for example.

The spectral sensitiser or a combination of spectral sensitisers can be added before, during or after the preparation of the emulsion.

Information on the usual colour couplers is to be found in Research Disclosure 37254, Part 4 (1995), page 288, and in Research Disclosure 37038, Part II (1995), page 80. The maximum absorption of the dyes formed from the couplers and from the colour developer oxidation product preferably falls within the following ranges: yellow couplers 430 to 460 nm, magenta couplers 540 to 560 nm, cyan couplers 630 to 700 mn.

In order to improve sensitivity, granularity, sharpness and colour separation, compounds are frequently used in colour photographic films which on reaction with the developer oxidation product release compounds which are photographically active, e.g. DIR couplers, which release a development inhibitor.

Information on compounds such as these, particularly couplers, is to be found in Research Disclosure 37254, Part 5 (1995), page 290, and in Research Disclosure 37038, Part XIV (1995), page 86.

The colour couplers, which are mostly hydrophobic, and other hydrophobic constituents of the layers also, are usually dissolved or dispersed in high-boiling organic solvents. These solutions or dispersions are then emulsified in an aqueous binder solution (usually a gelatine solution), and after the layers have been dried are present as fine droplets (0.05 to 0.8 mm diameter) in the layers.

Suitable high-boiling organic solvents, methods of introduction into the layers of a photographic material, and other methods of introducing chemical compounds into photographic layers, are described in Research Disclosure 37254, Part 6 (1995), page 292.

The light-insensitive intermediate layers which are generally disposed between layers of different spectral sensitivity may contain media which prevent the unwanted diffusion of developer oxidation products from one light-sensitive layer into another light-sensitive layer which has a different spectral sensitivity.

Suitable compounds (white couplers, scavengers or DOP scavengers) are described in Research Disclosure 37254, Part 7 (1995), page 292, and in Research Disclosure 37038, Part III (1995), page 84.

The photographic material may additionally contain compounds which absorb UV light, brighteners, spacers, filter dyes, formalin scavengers, light stabilisers, antioxidants, $D_{Min}$-dyes, additives for improving the dye-, coupler- and white stability and to reduce colour fogging, plasticisers (lattices), biocides and other substances.

Suitable compounds are given in Research Disclosure 37254, Part 8 (1995), page 292, and in Research Disclosure 37038, Parts IV, V, VI, VII, X, XI and XIII (1995), pages 84 et seq.

The layers of colour photographic materials are usually hardened, i.e. the binder used, preferably gelatine, is crosslinked by suitable chemical methods.

Suitable hardener substances are described in Research Disclosure 37254, Part 9 (1995), page 294, and in Research Disclosure 37038, Part XII (1995), page 86.

After imagewise exposure, colour photographic materials are processed by different methods corresponding to their character. Details on the procedures used and the chemicals required therefor are published in Research Disclosure 37254, Part 10 (1995), page 294, and in Research Disclosure 37038, Parts XVI to XXIII (1995), page 95 et seq., together with examples of materials.

EXAMPLES

Example 1

Production example

Preliminary product 1: benzo[1,2,4]thiadiazine-3-acetic acid (2-hexyl)decyl ester:

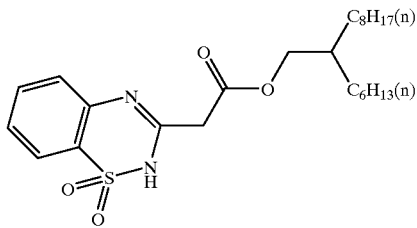

26.8 g benzo[1,2,4]thiadiazine-1,1-dioxide-3-acetic acid ethyl ester and 26.6 g 2-(n-hexyl)-decanol were heated to 170° C. in 10 ml o-dichlorobenzene for 4 hours whilst passing nitrogen over the batch. The solvent was subsequently volatilised under high vacuum, and the batch was taken up in toluene and chromatographed over 300 g silica gel using toluene and increasing proportions of dichloromethane as the mobile phase. After concentrating the polar eluates by evaporation, 39 g of a colourless crystalline material were obtained therefrom which melted at 87 to 90° C. and which coupled with colour developer/alkaline persulphate solution to produce an orange colour.

Preliminary product 2: benzo[1,2,4]thiadiazine-1,1-dioxide-3-isonitrosoacetic acid (2-hexyl)decyl ester:

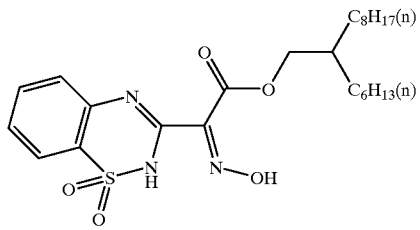

23.2 g of preliminary product 1 were placed in 160 ml acetic acid, and 7.0 g sodium nitrite were added with stirring at 10 to 20° C. so that there was negligible evolution of nitrous gases. The batch was stirred for a further 30 minutes at room temperature, was treated with iced water and was stirred until crystallisation was complete. The product was filtered under suction and dried in air. 20 to 22 g were obtained of a solid which melted at 137 to 140° C.

Preliminary product 3: benzo[1,2,4]thiadiazine-1,1-dioxide-3-formamidoacetic acid (2-hexyl)decyl ester:

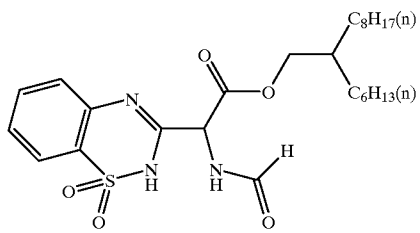

20 g preliminary product 2 were taken up in 150 ml formic acid and were heated under reflux whilst adding 20 g zinc dust in small portions. After 1 hour, the product was separated from the zinc dust by decantation, treated with 1000 ml of iced water and extracted three times with 200 ml dichloromethane each time. The extracts were neutralised with water and bicarbonate solution and were concentrated by evaporation. The wax-like residue was processed further without purification.

Coupler IRC-2:

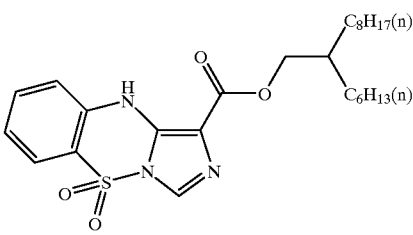

The residue of preliminary product 3 which remained after evaporation was taken up in 150 ml toluene, 50 ml phosphoryl chloride were added, and the batch was heated for 1 hour under reflux. The batch was allowed to cool to room temperature, and the solution was poured without cooling into 300 ml water to await the strongly exothermic hydrolysis of the excess phosphoryl chloride. The batch was maintained for a further 15 minutes at 65 to 70° C., and the toluene phase was separated, washed three times with 100 ml water each time, dried over magnesium sulphate, and chromatographed over 250 g silica gel. 16.5 g of the coupler, which had a melting point of 89 to 91° C., were obtained from the eluates by evaporation and crystallisation from methanol. On the thin layer chromatogram the coupler exhibited a pale cyan coupling with colour developer and alkaline persulphate solution.

The $^1$H NMR spectrum showed the following in the region of the aromatic and acidic protons:
a singlet (NH) at 9.1 ppm,
a doublet at 7.95 and 8.0 ppm
a singlet at 7.84 ppm,
a triplet at 7.62–7.74 ppm and an unresolved signal (A-B system+single proton) at 7.18–7.35 ppm.

The proposed structure was verified on the basis of NOE difference measurements.

Example 2 example of use

A red-sensitive partial layer structure was produced by depositing the following layers in the given sequence on a transparent film base made of cellulose triacetate. The quantitative data are given per m². The red-sensitised silver halide emulsion was stabilised with 0.1 g 4-hydroxy-6-methyl-1,3,3a,7-tetraazaindene with respect to 1 mole silver nitrate.

Layer structure 1.1.:

| layer 1: | (antihalo layer) |
|---|---|
|  | a black colloidal silver sol comprising |
|  | 0.2 g AgNO$_3$ |
|  | 1.1 g gelatine |
| layer 2: | (micrate intermediate layer) |
|  | AgBr-micrate emulsion (average grain diameter 0.07 μm) comprising |
|  | 0.25 g AgNO$_3$ |
|  | 1.0 g gelatine |
| layer 3: | red-sensitive layer (cubic silver bromide crystals with an average grain diameter of 0.5 μm) comprising |
|  | 5.35 g AgNO$_3$ |
|  | 3.5 g gelatine |
|  | 1.3 g cyan coupler C-1 |
|  | 1.2 g tricresyl phosphate. |

| | -continued |
|---|---|
| layer 4: | (hardener) |
| | 0.6 g gelatine |
| | 0.73 g instant hardener SHM-1 |

Coupler C-1

SHM-1 layer structure 1.2.:

| layer 1 | (antihalo layer) |
|---|---|
| | a black colloidal silver sol comprising |
| | 0.2 g AgNO$_3$ |
| | 1.1 g gelatine |
| layer 2 | (micrate intermediate layer) |
| | AgBr-micrate emulsion (average grain diameter |
| | 0.07 μm) comprising |
| | 0.25 g AgNO$_3$ |
| | 1.0 g gelatine |
| layer 3 | red-sensitive layer comprising |
| | 4.5 g AgNO3 |
| | 3.0 g gelatine |
| | 1.1 g coupler IRC-2 according to the invention |
| | 1.3 g tricresyl phosphate. |
| layer 4 | (hardener) |
| | 0.55 g gelatine |
| | 0.73 g instant hardener SMM-1 |

After casting, samples were exposed to daylight, behind an orange filter and a graduated neutral wedge filter, and were subsequently processed using the process described in "The British Journal of photography" 1974, page 597.

A cyan image was obtained from samples with layer structure 1.1 (=comparison), and an image with a slight brownish colour, with an absorption maximum at 740 nm, was obtained from those with layer structure 1.2 (according to the invention). In the case of coupler IRC-2 according to the invention, in the form of incorporation described above the main absorption was shifted into the infrared region to such an extent that there was practically no visual impression of colour. The slightly brownish hue was due to a weak secondary absorption at 470 nm.

I claim:

1. A color photographic silver halide material comprising at least one blue-sensitive silver halide emulsion layer which contains at least one yellow coupler, at least one green-sensitive silver halide emulsion layer which contains at least one magenta coupler, and at least one red-sensitive silver halide emulsion layer which contains at least one cyan coupler, wherein a compound of formula (I) is associated with the red-sensitive layer,

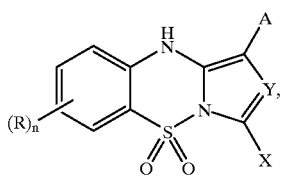

(I)

wherein

A denotes an electron acceptor group with a $\sigma_{p\text{-}}$ value of >0.25, R denotes a substituent, n denotes 0, 1, 2, 3 or 4, Y denotes N or C—CN, and X denotes H or a group which is separable during chromogenic coupling.

2. The color photographic silver halide material according to claim 1, wherein Y represents N.

3. The color photographic silver halide material according to claim 1, wherein X represents H, a halogen, an alkoxy, aryloxy, hetaryloxy, acyloxy, sulphonyloxy, alkoxycarbonyloxy, aryloxycarbonyloxy, alkylthio, arylthio, hetarylthio, alkoxycarbonylthio, acylalkylamino, alkoxycarbonylamino, N-alkylsulphonamido, aryloxycarbonylamino, carboxy substituent, a heterocyclic radical which is bonded via a nitrogen atom, an arylazo, hetarylazo group or the residue of a photographically active compound.

4. The color photographic silver halide material according to claim 1, wherein A represents an alkoxycarbonyl, carbamoyl or cyano group.

5. The color photographic silver halide material according to claim 1, wherein (R)$_n$ represents —CN, —Cl, —OR$^1$, —NR$^2$CO—OR$^1$, —CONH R$^1$, —COO R$^1$ or S R$^1$, with the proviso that R$^1$ represents an alkyl, aryl, arylene, hetaryl or hetarylene group and R$^2$ represents H or an alkyl radical.

6. The color photographic silver halide material according to claim 1, wherein n represents 0, 1 or 2.

7. The color photographic silver halide material as claimed in claim 6, wherein A represents an alkoxycarbonyl, carbamoyl or cyano group.

8. The color photographic silver halide material according to claim 3, wherein A represents an alkoxycarbonyl, carbamoyl or cyano group.

9. The color photographic silver halide material as claimed in claim 7, wherein R represents —CN, —Cl, —OR$^1$, —NR$^2$CO—O R$^1$, —CONH R$^1$, —COO R$^1$ or S R$^1$, with the proviso that R$^1$ represents an alkyl, aryl, arylene, hetaryl or hetarylene group and R$^2$ represents H or an alkyl radical, and n represents 0, 1 or 2.

10. The color photographic silver halide material according to claim 8, wherein R represents —CN, —Cl, —OR$^1$, —NR$^2$CO—O R$^1$, —CONH R$^1$, —COO R$^1$ or S R$^1$, with the proviso that R$^1$ represents an alkyl, aryl, arylene, hetaryl or hetarylene group and R$^2$ represents H or an alkyl radical, and n represents 0, 1 or 2.

11. A photographic color development process which comprises exposing image by image a photographic material, which contains a compound of formula (I) in at least one silver halide emulsion

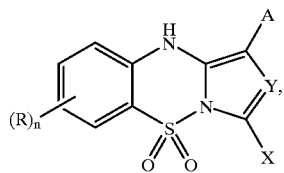

(I)

wherein
- A denotes an electron acceptor group with a $\sigma_{p\text{-}}$ value of >0.25,
- R denotes a substituent,
- n denotes 0, 1, 2, 3 or 4
- Y denotes N or C—CN, and
- X denotes H or a group which is separable during chromogenic coupling, and developing with a color developer compound of a phenylenediamine or diaminotoluene type or a mixture thereof.

12. The photographic development process according to claim 11, wherein said photographic material is developed with CD 3.

13. The photographic color development process as claimed in claim 12, wherein the compound of formula (I)

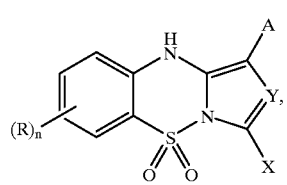

(I)

where

Y is N,

X represents H, a halogen, an alkoxy, aryloxy, hetaryloxy, acyloxy, sulphonyloxy, alkoxycarbonyloxy, aryloxycarbonyloxy, alkylthio, arylthio, hetarylthio, alkoxycarbonylthio, acylalkylamino, alkoxycarbonylamino, N-alkylsulphonamido, aryloxycarbonyl amino, carboxy substituent, a heterocyclic radical which is bonded via a nitrogen atom, an arylazo, hetarylazo group or the residue of a photographically active compound, A represents an alkoxycarbonyl, carbamoyl or cyano group, R represents —CN, —Cl, —OR$^1$, —NR$^2$CO—O R$^1$, —CONH R$^1$, —COO R$^1$ or S R$^1$, with the proviso that R$^1$ represents an alkyl, aryl, arylene, hetaryl or hetarylene group and R$^2$ represents H or an alkyl radical, and n represents 0, 1 or 2.

\* \* \* \* \*